United States Patent [19]
Fullmer et al.

[11] Patent Number: 5,968,034
[45] Date of Patent: Oct. 19, 1999

[54] PULSED FILAMENT LAMP FOR DERMATOLOGICAL TREATMENT

[75] Inventors: David J. Fullmer; David R. Hennings, both of Auburn; Bruce J. Sand, Beverly Hills, all of Calif.

[73] Assignee: Laser Aesthetics, Inc., Auburn, Calif.

[21] Appl. No.: 09/103,756

[22] Filed: Jun. 24, 1998

Related U.S. Application Data

[63] Continuation-in-part of application No. 08/881,539, Jun. 24, 1997, Pat. No. 5,885,274.

[51] Int. Cl.$^6$ ..................................................... A61B 17/36
[52] U.S. Cl. ..................................... 606/9; 606/3; 606/13
[58] Field of Search ........................................ 606/9, 3, 13

[56] References Cited

U.S. PATENT DOCUMENTS

| | | | |
|---|---|---|---|
| 3,630,203 | 12/1971 | Sellinger et al. | 128/303 |
| 3,867,948 | 2/1975 | Kallenborn | 128/395 |
| 4,376,376 | 3/1983 | Gregory | 62/51 |
| 4,976,709 | 12/1990 | Sand | 606/5 |
| 5,020,995 | 6/1991 | Levy | 433/215 |
| 5,057,104 | 10/1991 | Chess | 606/9 |
| 5,098,428 | 3/1992 | Sandlin et al. | 606/22 |
| 5,137,530 | 8/1992 | Sand | 606/5 |
| 5,344,418 | 9/1994 | Ghaffari | 606/9 |
| 5,358,503 | 10/1994 | Bertwell et al. | 606/27 |
| 5,405,368 | 4/1995 | Eckhouse | 607/88 |
| 5,511,563 | 4/1996 | Diamond | 128/848 |
| 5,595,568 | 1/1997 | Anderson et al. | 606/9 |
| 5,624,435 | 4/1997 | Furumoto et al. | 606/10 |
| 5,683,380 | 11/1997 | Eckhouse et al. | 606/9 |
| 5,810,801 | 9/1998 | Anderson et al. | 606/9 |
| 5,814,040 | 9/1998 | Nelson et al. | 606/9 |

OTHER PUBLICATIONS

Anvari et al., Selective cooling of biological tissues: application for thermally mediated therapeutic procdures, Phys. Med. Biol. 40, pp. 241–252, 1995.

Jacques, S.L.; Wang, L., Monet Carlo modeling of light transport in tissues: Optical–Thermal Response of Laser–Irradiated Tissue, Plenum Press, N.Y., pp. 73–100, 1995.

Lask et al, Nonablative Laser Treatment of Facial Rhytides; Proc. SPIE, vol. 2970, 1997.

Abstract 187: "Long pulsed ruby laser for hair removal: Comparison between different spot sizes, temperatures and interva between first and second treatment," Lasers in Surgery and Medicine, Proceedings of the American Society for Laser Medicine and Surg, 1998.

Anvari et al., Selective cooling of biological tissues: application for thermally mediated therapeutic procedures, Phys. Med. Biol. 40 (1995) 241–252.

Lask et al., Nonblative Laser Treatment of Facial Rhytides: Proc. SPIE, vol. 2970 (1997, to be published).

Jacques SL, Wang L. Monte Carlo modeling of light transport in tissues: Opitcal–Thermal Response of Laser–Irradiated Tissue. (Plenum Press, New York, 1995), pp. 73–100.

Abstract 187: "Long Pulsed Ruby laser for Hair Removal; Comparison between Different Spot Sizes, Temperatures and Interval Between First and Second Treatment", Lasers in Surgery and Medicine, Proceedings of the American Society for Laser Medicine and Surgery 18$^{th}$ Annual Meeting in San Diego, California, Apr. 5–7, 1998. (Applicant is aware of an audio tape recording of the oral presentation.)

*Primary Examiner*—Michael Buiz
*Assistant Examiner*—Julian W. Woo
*Attorney, Agent, or Firm*—Ray K. Shahani, Esq.

[57] ABSTRACT

A high energy filament lamp light source, such as a quartz tungsten halogen lamp, operated in a pulsed mode with a high voltage input, creates a particular energy output. Applications of such apparatus and methods include treatment of the dermis and/or sub-epidermal tissues for the purpose of skin recontouring, thermal destruction of hair follicles for the purpose of hair removal, and others, and a method which selectively preheats a subsurface region in targeted tissue to sub-thermal modification threshold values without significant heat damage to surrounding layers prior to further treatment.

39 Claims, 3 Drawing Sheets

PULSED FILAMENT LAMP FOR DERMATOLOGICAL TREATMENT

RELATED INVENTIONS

This application is a continuation-in-part of Applicant's applications Ser. No. 08/881,539, filed Jun. 24, 1997, now U.S. Pat. No. 5,885,274 entitled Pulsed Filament Lamp for Dermatological Treatment.

FIELD OF THE INVENTION

The present invention relates generally to modification of dermatological and other collagen containing tissue using non-laser infrared light energy. More particularly, the invention relates to the use of a high energy, pulsed incandescent-type filament lamp, such as a quartz tungsten halogen lamp, operated in a pulsed mode with a high voltage input, to create a particular energy output. Applications of such apparatus and methods include treatment of the dermis and/or sub-epidermal tissues for the purpose of skin recontouring, thermal destruction of hair follicles for the purpose of hair removal, and others.

BACKGROUND OF THE INVENTION

Electromagnetic energy has been widely used in medical applications for a very long time. With the advent of lasers, such applications have included tissue removal and shrinkage, tissue welding, etc.

The use of lasers for cosmetic surgery by dermatologists and plastic surgeons is expanding rapidly. Despite the fact that reimbursement for these procedures is often not covered under third-party payer health plans, other socioeconomic factors seem to be driving the increased demand for these services. Such procedures include laser dosimetry to safely treat and remove vascular lesions (port wine stain and other red marks), benign pigmented lesions (brown marks) and in some cases, tattoo markings from skin surfaces. These procedures, though recently developed, are highly controllable and well known.

Collagen is the single most abundant animal protein in mammals, accounting for up to 30% of all proteins. The collagen molecule, after being secreted by the fibroblast cell, assembles into characteristic fibers responsible for the functional integrity of tissues making up most organs in the body. The skin is the largest organ of the body occupying the greatest surface area within the human body. As age advances and as a result of other noxious stimuli, such as the increased concentration of the ultraviolet part of the electromagnetic spectrum as radiated from the sun, structural integrity and elasticity of skin diminishes.

Facial rhytides (e.g., periorbital and perioral wrinkles produced by photodamage and/or aging) have previously been treated using a variety of modalities, including dermabrasion, chemabrasion (chemical peel), and $CO_2$ laser skin resurfacing (LSR)—a technique in which pulsed or scanned $CO_2$ laser light at 10.6 microns wavelength is used to ablate skin. All three modalities provoke a strong skin wound healing response that leads to wrinkle reduction—it is thought that the synthesis of new collagen essentially recontours the overlying skin surface.

Unwanted hair is a common dermatological and cosmetic problem, and can be caused by heredity, malignancy or endocrinological disease. Hair can be temporarily removed using wax epilation, depilatory creams and shaving. Permanent hair removal currently involves electrolysis, or the insertion of a current carrying needle into each hair follicle. Hair removal and the destruction of the generating follicle results from a traumatic episode within the hair follicle itself.

$CO_2$ LSR has recently emerged as a widely used aesthetic surgical modality which may have advantages of improved reproducibility and control compared to dermabrasion and chemabrasion. However, $CO_2$ LSR is often accompanied by complications such as persistent erythema, hyperpigmentation, hypopigmentation, scarring and infection. Patients also experience edema, drainage, and burning discomfort during, typically, the first few weeks after treatment. The present invention is directed toward treating facial rhytides using a new nonablative non-laser modality that may be effective in reducing both the severity of wrinkles and the incidence of morbidity presently associated with LSR Previous disclosures, such as U.S. Pat. No. 4,976,709 and U.S. Pat. No. 5,137,530 have described methods and apparatus for achieving controlled shrinkage of collagen tissue. These prior inventions have applications to collagen shrinkage in many parts of the body and describe specific references to the cosmetic and therapeutic contraction of collagen connective tissue within the skin. In the early 1980's it was found that by matching appropriate laser exposure parameters with these conditions, one had a novel process for the nondestructive thermal modification of collagen connective tissue within the human body to provide beneficial changes. The first clinical application of the process was for the non-destructive modification of the radius of curvature of the cornea of the eye to correct refractive errors, such as myopia, hyperopia, astigmatism and presbyopia. New studies of this process for the previously unobtainable tightening of the tympanic membrane or ear drum for one type of deafness have been made.

It is with this motivation that applications of collagen modulation have been driven. These techniques are intended to accomplish the same wrinkle removal without the usually attendant trauma and associated wound healing responses or inflammatory response. However, several drawbacks to the clinical use of medical lasers exist, including high initial costs of $50,000–150,000 and significant annual maintenance costs. Lasers are dangerous and require extensive training of personnel to avoid injury in the operating room. Furthermore, multi-wavelength operation with a typical laser system is impossible, and those systems offering multi-wavelength operation are more expensive and more complicated to operate. Finally, the efficiency of most laser systems is very low, and a very low amount of infrared energy is typically created within an operable wavelength domain, compared to the amount of energy required to drive the laser.

U.S. Pat. No. 5,595,568 issued Jan. 21, 1997 to Anderson et al. teaches permanent hair removal using optical pulses. The use of a medical laser is contemplated in conjunction with a rounded or flat probe for contacting the hairs to be removed and for transmitting heat through the skin layer to the follicles of the undesired hairs.

Utilization of non-laser electromagnetic energy for therapeutic and/or aesthetic treatment has been limited. One such use is taught in U.S. Pat. No. 5,344,418 issued Sep. 6, 1994 to Ghaffari, an optical system for treatment of vascular lesions. The invention teaches the use of a mercury vapor arc lamp with a wavelength domain of between 480 and 600 nanometers in conjunction with a passive cooling lens. The cooling lens is placed directly onto the surface of the skil, with cooling solution or fluid circulated on the opposite side of the lens, to prevent overheating of the surface layer of tissue.

Another invention utilizing non-coherent light is taught in U.S. Pat. No. 5,405,368 issued Apr. 11, 1995 to Eckhouse, which teaches a method and apparatus for therapeutic electromagnetic treatment. The device comprises a housing and an incoherent light source such as a flashlamp, operable to provide a pulsed light output for treatment, the device having a housing, reflector, light filter and a pulse forming circuit. The method of treatment includes steps of providing a high power, pulsed light output from a non-laser light source and directing the pulsed light output to a treatment area, with control of pulse width and filtration. The flashlamp used is gas filled and the domain of the output wavelength is within the visible range, i.e. 500–650 nanometers.

In both of the cited prior art documents, the emphasis is the use of non-laser energy for targeting blood vessels. They both strive to remove or reduce the infrared component of the light as it interferes with the treatment of blood vessels. Furthermore, neither gas filled flashlamps nor mercury-xenon arc lamps contain enough infrared output to be useful for the thermal modification of collagen.

Attempts to treat targeted regions within tissue such as vascular tissue have resulted in undesirable heating in the tissue surrounding the targeted tissue. The addition of cooling devices have resulted in removing heat from the tissue surrounding the targeted tissue, however this results in additional energy requirements because the targeted tissue is also cooled by the cooling device resulting in lower pretreatment temperature. The resulting increase in treatment energy may mostly counter act the cooling device and reducing its benefit while placing a greater demand on the treatment energy source.

ADVANTAGES AND SUMMARY OF THE INVENTION

Therefore, it is an advantage and an objective of the present invention to provide a safe and economical method for the treatment of the dermis and/or the sub-epidermis for the purpose of skin recontouring and the thermal destruction of hair follicles for the purpose of hair removal.

It is also an advantage and an objective of the present invention to provide such a system comprising a pulsed, incandescent or filament lamp, non-laser light source with a high energy output which maxinizes the infrared domain of the electromagnetic spectrum. Providing a pulsed filament or other incandescent lamp as the source of light energy is novel and unique. The use of a filament or incandescent lamp in a pulsed mode is heretofore unknown and provides unexpected results. Pulsing the lamp provides a device with a higher peak energy output, with an essentially equivalent or higher or lower average power rating as available or taught in the prior art. The effect on tissue is greater compared to the effect of irradiation with a continuous light source at the same average power output of the lamp.

Yet another advantage of the present invention is to provide an improved system for creating selective temperature profiles in material such as tissue.

Yet another advantage of the present invention is to provide such a system which selectively preheats a subsurface region in tissue, such as tissue targeted for further thermal treatment.

Yet another advantage of the present invention is to reduce the level of pulsed energy needed for treatment by preheating at least one portion of the targeted tissue with a low energy light source.

Yet another advantage of the present invention is to provide such a system which selectively preheats a subsurface region in targeted tissue to sub-thermal modification threshold values without significant heat damage or other thermal modifications to surrounding layers prior to further treatment.

Yet another advantage of the present invention is to provide such a system which selectively preheats a subsurface region in tissue to cause a temperature profile which results in thermal changes in the selected or targeted region without undesirable thermal changes in layers surrounding the selected region.

Yet another advantage of the present invention is to provide such a system which selectively preheats a subsurface layer in tissue to cause collagen shrinkage or thermal damage in skin.

Yet another advantage of the present invention is to provide such a system which selectively preheats a subsurface region of vascular tissue.

Yet another advantage of the present invention is to provide such a system which selectively preheats a subsurface region of tissue which contains hair follicles.

In summary, a preferred embodiment of the present invention comprises a pulsed quartz tungsten halogen lamp with a solid filament, or other similar near-black body radiator, with a high infrared component output. An electronic circuit drives the lamp at very high powers for very short periods of time to provide an output with high energy densities. A lamp filament with associated simmer circuit is optionally provided to keep the filament at a higher temperature between pulses, thus resulting in a lamp with more efficient power conversion characteristics.

Additional benefits of the present invention are: (1) the system is simpler and less complicated than a laser system; (2) the system is safer, more economical and requires less maintenance than a laser system; (3) enhanced multi-wavelength photonic-tissue interaction; and (4) provides maximum infrared radiation efficiency relative to the input energy, typically in the range of between about 700 and about 1800 nanometers.

The tissue may be preheated with any operative heating device such as, but not limited to, any intense light source, a gas discharge or other flashlamp, a filament or other incandescent lamp, a laser diode or other laser source, electrical current, radiofrequency waves, microwaves, ultrasound or other source of electromagnetic energy which penetrates into regions of tissue, by conduction or convection as with a forced air blower, contact device, active or passive heating means, etc., beneath the surface such that the preheating occurs simultaneously or just prior to the pulsed treatment application of energy from the energy delivery device, thus preferentially preheating a region of tissue without excessive or otherwise undesirable heating of or effect on surrounding tissue.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENT

Preferred Apparatus

It will be understood that while numerous preferred embodiments of the present invention are presented herein, numerous of the individual elements and functional aspects of the embodiments are similar. Therefore, it will be understood that structural elements of the numerous apparatus disclosed herein having similar or identical function will have like reference numerals associated therewith.

Figure 1:
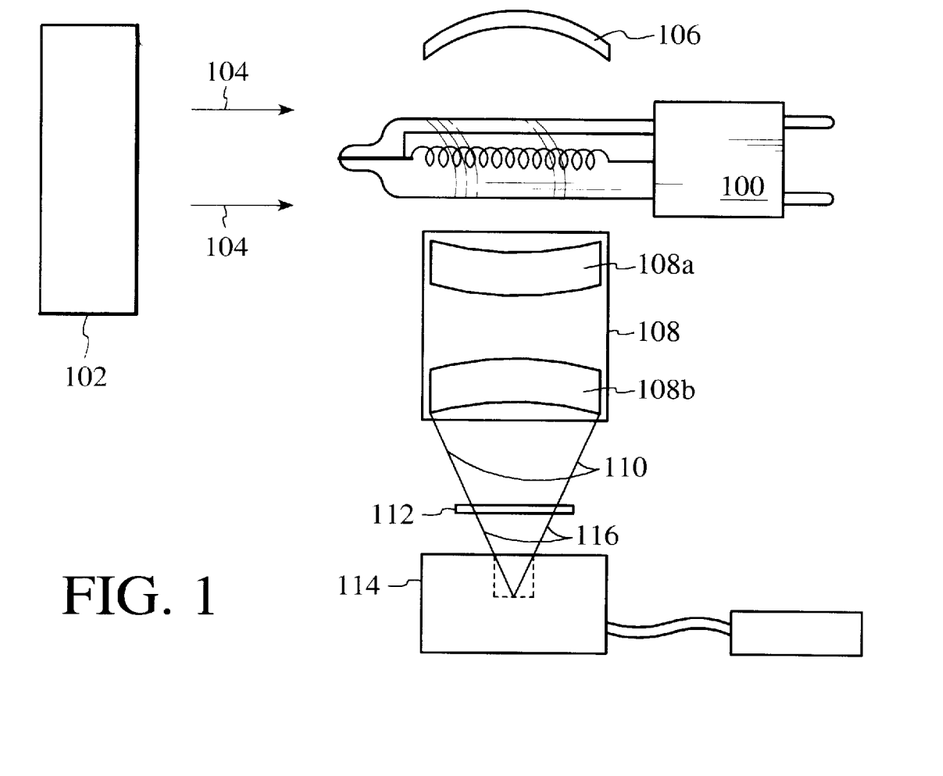
FIG. 1 is a representative schematic view of the filament lamp and optics of a preferred embodiment of the present invention in a test configuration.

FIG. 1 is a representative schematic view of the filament lamp and optics of a preferred embodiment of the present invention in a test configuration. The filament lamp 100 can be selected from any which meets the stringent criteria of the present invention. The filament lamp should have a strong output in the wavelength domain of between about 700 and about 1800 nanometers, this broad-band transmission characteristic of near-black body radiators. A suitable filament lamp 100 is the tungsten quartz halogen (TQH) type lamp model 6315 manufactured by ORIEL, INC. of Stratford, Conn. This lamp is rated at 1000 watts, is specified for operation at 120 VDC, generates up to approximately 27,500 lumens of flux and has a filament size of about 6.0 mm wide and about 16 mm long. Overall, the lamp is about 0.75 inches (19 mm) diameter and about 4.10 inches (104 mm) long.

It will be understood that any suitable lamp may be used. Although generally intended for continuous use, incandescent lamps such as the QTH or any other lamp which supplies black body-type infrared radiation across a spectrum or predetermined wavelength domain or bandwidth can be used. Additionally and alternatively, the term "non-coherent" light is used to mean non-laser, broad spectrum electromagnetic radiation.

It will be understood that the incandescent lamp, as invented by Thomas Edison, U.S. Pat. No. 223, 898 (hereby expressly incorporated herein), along with essentially all of the improvements, modifications, additions and enhancements thereto and since then, are embodiments of the filament lamp of the present invention. It will be understood that the filament lamp of the present invention produces light energy based upon a flow of electricity through a filament, and improvements thereon include the use of a tungsten filament, the introduction of small traces of halogen gas into the lamp enclosure, any of various envelope and socket designs, and improved and ever increasingly improving materials and methods of construction.

The filament lamp 100 is cooled by a small fan 102 which blows a stream of air or other coolant fluid across the lamp and associated optics in general direction 104. On one side of the filament lamp 100 there is a straight, curved or otherwise focusing reflective element 106, such as a silvered mirror. Electromagnetic energy radiating from the filament lamp 100 and reflected off reflective element 106 is directed through collimating lens 108. A typical collimating lens 108 is comprised of two individual lens elements 108a and 108b, each with a diameter of about 1.75 inches and separated by a short distance such that the collimating lens 108 has a thickness of about 1.5 inches.

Optionally, the collimated electromagnetic energy 110 is transmitted through a conversion filter 112. A typical conversion filter 112 is made of ionically colored glass and has a certain transmittance value, depending upon the wavelength of incident light. Typical conversion filters 110 can be made of FG3, KG2, KG3, RG9 or RG1000 type glass manufactured by Schott Glaswerke of Mainz, Germany. It will be understood that any filter means, including any optical glass, optical lenses, or other optical equipment including controllable and adjustable optical filters, to allow only the spectrum desired to reach the target tissue, will be suitable for use with the present invention.

For test purposes, a detection meter 114 is placed such that the filtered light 116 emanating from conversion filter 112 will impinge thereon. Slight clipping of the side rays will have negligible effect upon the resultant measurements.

Figure 2:
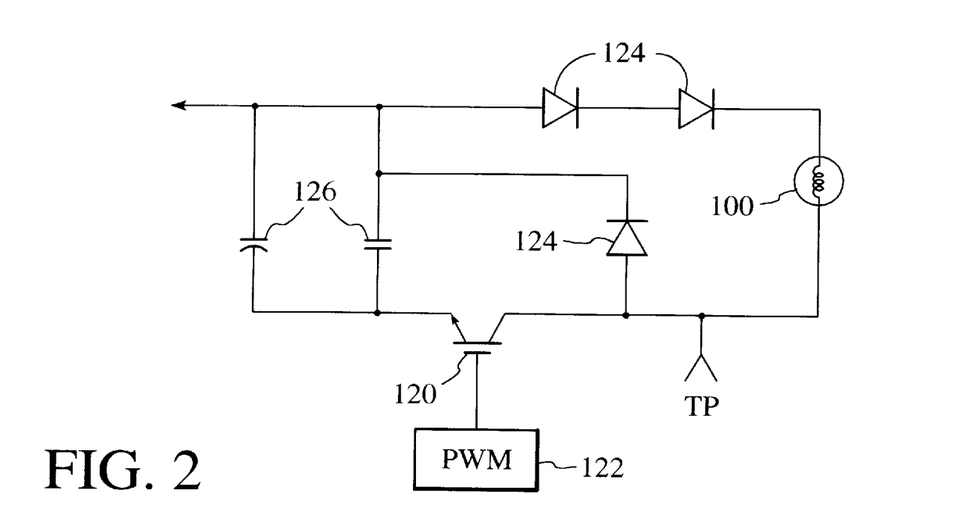
FIG. 2 is a representative schematic view of the drive circuit for the filament lamp of a preferred embodiment of the present invention.

FIG. 2 is a representative schematic view of the drive circuit for the filament lamp of a preferred embodiment of the present invention. The drive circuit is comprised, at least in part, of the filament lamp 100 in series with an high power switching device 120. Such switching device 120 could be an insulated gate bipolar transistor-type (IGBT) switch or other suitable switching device, which allows the use of high current/short pulse circuitry. The switching device 120 is controlled by pulse width modulator (PWM) 122 and pulse width can be adjusted between at least about 10 and about 1000 milliseconds to match the thermal relaxation time of the target tissue for selective photothermolysis or other thermal/optical effect.

Various diodes 124 are placed in the circuit for performing damping functions. Additionally, one or more capacitors 126 form part of the circuit and serve to collect and store energy until such time as the circuit is closed by activation of switching device 120 and the filament lamp 100 is energized. Such capacitors 126 result in a circuit having, in a preferred embodiment, a total of about 10,000 microfarads capacitance. Additionally, at least one test point, such as $TP_1$, is configured into the circuit.

Figure 3:
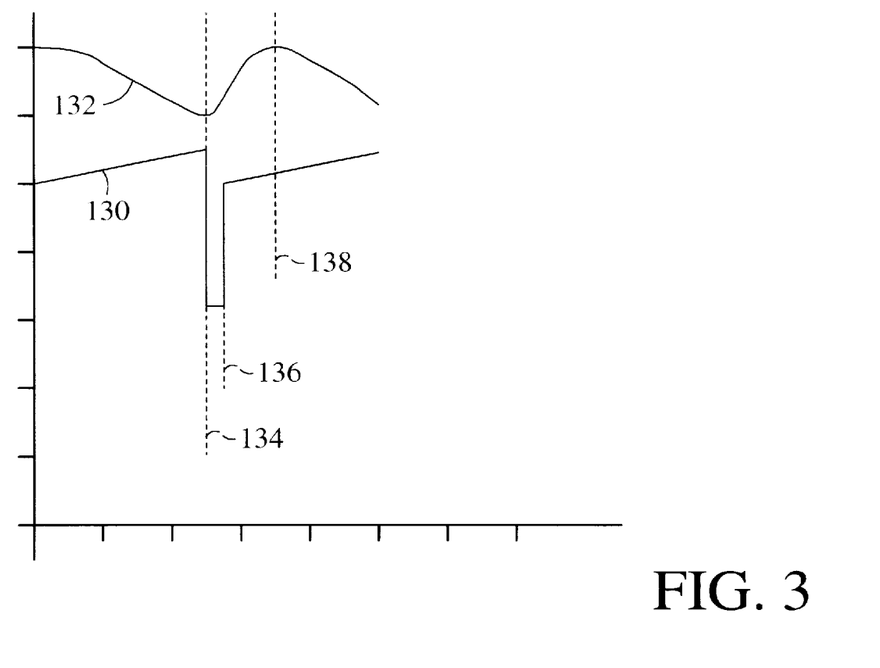
FIG. 3 is a representative schematic view of the input voltage and resultant waveform oscilloscope trace produced by the filament lamp circuit and optics of a preferred embodiment of the present invention.

FIG. 3 is a representative schematic view of the input or applied voltage 130 and resultant waveform 132 oscilloscope trace produced by the filament lamp circuit and optics of a preferred embodiment of the present invention. A typical detection meter 114 is model number J9-355 made by Molectron, Inc. of Portland, Oreg. A typical calibration factor for such detection meter 114 is about 0.25 volts/Joule at a single wavelength transmission of about 2.1 microns.

The circuit potential 130 across the capacitors, in volts, is observed to increase slowly, ramping up until the filament lamp is fired at time point 134. A pulse width of 53 milliseconds is used and the capacitors are discharged. Following the 53 millisecond time period, the circuit potential 130 is again observed to begin a slow increase starting at time point 136. A short time thereafter, the voltage output of the photo detector is observed to peak at time point 138, thus indicating a response or delay time between the energization of the filament lamp and output from the detector 122.

The following table demonstrates the range of some of the experimentally obtained data from the system shown in FIGS. 1 and 2. Such data is preliminary and, as such, it is expected that actual results may vary within as well as outside of the given ranges.

TABLE 1

J9-355 Test Results

| Applied Potential (volts DC) | Peak Output (volts DC) | Peak Output (Total Joules) | Pulse Width (milliseconds) |
|---|---|---|---|
| 150–231 | 0.043–0.246 | 0.175–0.984 | 53 |

Figure 4:
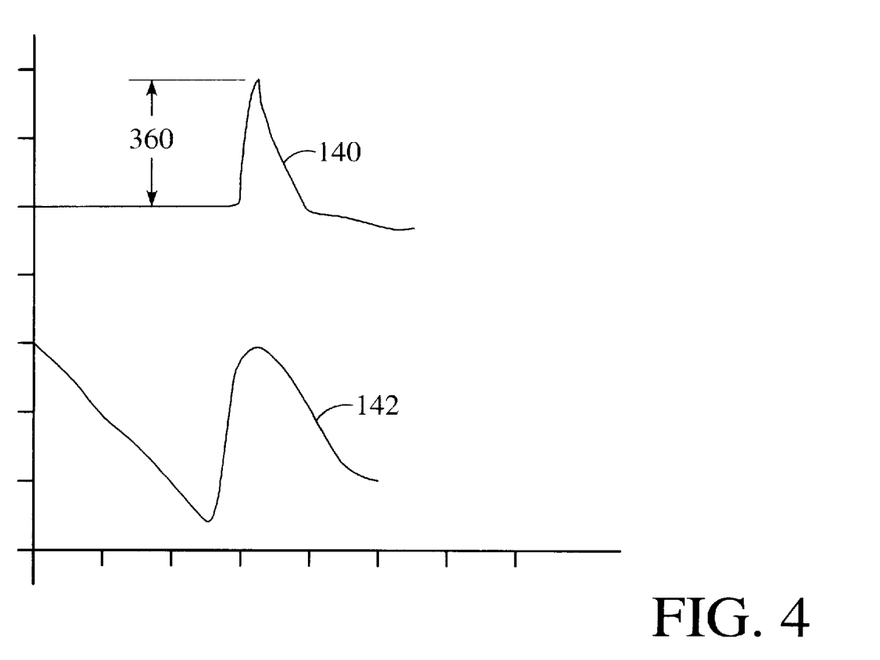
FIGS. 4 and 5 are representative schematic views of input voltage and resultant waveform oscilloscope traces produced by the filament lamp circuit and optics of preferred embodiments of the present invention, FIG. 5 that of a preferred embodiment of the present invention with tissue preheating.

FIG. 4 is another representative schematic view of the applied voltage and resultant voltage waveform oscilloscope trace produced by the filament lamp circuit and optics of a preferred embodiment of the present invention. The upper waveform 140 is a representative oscilloscope trace produced by an Eltec 420 detection meter manufactured by Eltec Corporation and the lower waveform 142 was produced by a Molectron J9-355. The upper waveform 140 was produced using about 200 volts DC on the lamp and the lower waveform 142 was produced with about 231 volts DC on the lamp. Both were created using a 78 millisecond pulse, as determined using a full width half maximum (FWHM). The Eltec meter resulted in 0.36 volts out and the Molectron meter produced 0.2468 volts out. One important distinction between the two meters is that the Eltec 420-4 has a relatively fast time constant (reacts rapidly to stimulus) compared to that of the Molectron J9-355.

The following table demonstrates the range of some additional experimentally obtained data from the system shown in FIG. 2. Again, such data is preliminary and, as such, it is expected that actual results may vary within as well as outside of the given ranges.

TABLE 2

Additional Test Results

| Voltage In | Watts Out | Calculated Joules out, corrected for Repetition Rate | End of Pulse Voltage | Joules Input |
|---|---|---|---|---|
| 100–330 | 0.78–9.00 | 0.531–3.91 | 62.5–181 | 40.0–195.53 |

Preferred Methodology
I. TREATMENT PARAMETERS

By overdriving the lamp for short periods of time it is possible to increase the output of the lamp for a short time duration. Normally operated in a continuous condition, its efficiency might be so low that as much as 90% of the total, or abut 900 watts, is wasted. The unique electronic drive circuit to pulse the lamp makes it practical as a medical device for dermatological and aesthetic applications. In a preferred embodiment of the methods of the present invention, the system drives the lamp at about 3 times its normal operating condition but does so for only about 10 to about 1000 milliseconds, or more or less.

The short pulses are enhanced when the filament of the lamp is held in a warm condition in the time periods between delivery of the main pulses. A "simmer" type circuit allows a faster rise time of the light pulse produced by the lamp.

Typically, densities of 0.1 to 30.0 joules/square centimeter have been found to be required for the us treatment of the dermis. Preclinical studies have shown that about 2.0 joules/square centimeter of human tissue are required. Pulse width can be adjusted between at least about 10 and about 1000 milliseconds to match te thermal relaxation time of the target tissue for selective photothermolysis or other thermal/optical effect. The energy emitted from the lamp is collected by a reflective surface and focusing optics. It has been found that a filter system can be configured to allow treatment of hair follicles with a light spectrum between about 700 and about 1000 nanometers. Filtered light mainly in a spectrum ranging from about 850 to about 1800 nanometers exposure with or without cooling, demonstrates thermal modification of other dermatological collagen.

For the purposes of the present invention, it will be understood that the term "non-homogeneous collagen" will refer to that collagen typically found in human or other animal skin. Non-homogeneous collagen is also anisotropic by nature, in that it does not exhibit identical properties (such as light transmission, birefringence, conductivity of heat or electricity) when measured along axes in different directions. It is well known that skin and dermatological tissue, as well as the tissue of hair follicles, is composed of such non-homogeneous collagen, as compared to other transparent, isotropic and homogeneous collagen-containing tissue such as stromal collagen of the cornea. Thus, treatment of dermatological tissue is most effective when the appropriate wavelength spectrum is selected from the broad infrared spectrum output of the light source to match the "effective optical transmission" characteristics of the target tissue. Effective optical transmission is the result of spectral absorption and anisotropic tissue scatter. Thus, the step of determining the optimum treatment pulse width is based on the thermal relaxation time, a function of effective optical transmission, of the target tissue.

II. DYNAMIC COOLING, HEAT SINK METHODOLOGY

Studies have shown that use of the tungsten filament lamp with an appropriate heat sink produce a optimum thermal profile for collagen shrinkage and hair removal. It has been shown that irradiating tissue with the infrared radiation through a surface thermal absorption element or heat sink permits an optimum thermal profile within the target tissue with near physiologic temperature at the surface of the irradiated surface, thus minimizing surface thermal damage. In the case of collagen shrinkage, this is clearly desirable. Attenuating the surface temperature before irradiation and creating a boundary layer on the skin surface results in selective cooling of the target tissue thus preserving the normal overlying epidermis.

Providing a glass or sapphire tip probe to the surface of the tissue being treated, while transparent to the radiation being delivered to the tissue, will act as an efficient and convenient heat sink for the surface layers of the skin.

Modem instruments to provide dynamic cooling of the surface layers of tissue are well suited to these applications. A preferred embodiment of such a device contains a focusing lens 44 and, optionally, other optics or mechanical equipment including a beam splitter, focusing knob and adjustable mounting means, thereby producing a focus spot on the surface of the tissue above the collagen to be treated. A coolant spray can be provided through the handpiece or it could be provided with another separate device. Finally, a connection to a computer and the filament lamp driver will allow the device to utilize electronic or other thermal sensing means and obtain feedback control signals for the handpiece. An optimum cooling strategy might be one that uses a short spurt of cryogenic liquid (e.g., 5–20 ms) to reduce the local temperature in the overlying epidermis, while minimizing attenuation of the filament lamp energy by the boundary layer, followed by post-irradiation cooling spurt that provides cooling or dissipation of the epidermal heat generated by absorption of energy in the non-isotropic skin, optionally containing various pigmentation levels. An appropriate cryogen spray would be tetrafluoroethane, $C_2H_2F_4$, an environmentally compatible, non-toxic, nonflammable freon substitute. In clinical application the distance between the aperture of the spray valve and the skin surface should be maintained at about 20 millimeters.

During a typical dynamic cooling process, the surface of the skin is pre-cooled to as low as 0 degrees Celsius or lower, at a rate fast enough to cool the surface only but not dissipate heat from below about 400–500 microns below the surface. In a preferred embodiment, during the cooling step the target tissue remains at body temperature and is not cooled at all. By applying cooling to the surface of the skin for a short period of time, typically between about 5 and 100 milliseconds and then delivering laser energy, the surface is initially cooled but the target tissue never is. Generally, the surface layer of skin is rapidly cooled. A high rate of cooling will prevent local and vicinal hypothermia and will also tend to have a numbing, anesthetic or analgesic effect. It will be understood that in at least one preferred embodiment of the method of the present invention, since only a relatively very thin outer layer of skin is cooled in a relatively very rapid period of time, laser energy must be applied either instantaneously with termination or dynamic or removal of passive cooling or essentially immediately thereafter. Therefore, upon delivery of laser energy onto the surface and therethrough, the target tissue will be raised to the optimal thermal shrinkage temperature and generally not any higher, in an adequately rapid process, with the surface temperature of the skin remaining unelevated from body temperature, or if elevated at all, not elevated to a temperature which would have any adverse effect on the tissue. Adverse effects of elevated tissue surface temperature include discomfort or pain, thermal denaturing of proteins and necrosis of individual cells at the surface only, or deeper tissue ablation potentially leading to hyperplasia, scaring, or hyperpigmentation, a proliferation of cells formed in response to the induced trauma. In a preferred embodiment of the method of the present invention, cooling and heating are performed in a predetermined timing sequence, optionally with the use of timer circuits and/or other controller means.

Thus, it will be obvious to those skilled in the art that a passive heat sink includes glass or sapphire tip probes, and other types of devices to lay on the surface of the skin. It will also be obvious that a dynamic type of heat sink will refer to those actively cooled by flowing gas or liquid, jets or spurts of coolant such as freon, and other active types of heat exchangers suitable for surface cooling while irradiating sub-surface portions of collagen tissue.

III. TARGET TISSUE PREHEATING

This invention is related to the method of warning the entire area of treatment to a temperature above normal, but below treatment levels in order to reduce the pulsed energy needed to ultimately treat the target tissue. Tissue is modified or destroyed at a generally fixed and known temperature that is usually independent of the starting, native, resting, natural, ambient temperature of the tissue. It is known that collagen will shrink at approximately 65 degrees C. Most methods of shrinking collagen deliver energy in a pulsed manner to raise the tissue from an initial temperature, such as the normal body temperature of 30 degrees, all the way to 65 degrees at one time. This temperature rise of 35 degrees requires energy sources capable of delivering up to 6 joules to elevate a 5 mm diameter spot. The present invention performs this same process in several steps.

In a first step, the target tissue is raised to a controlled, elevated, non destructive level, e.g., 40 degrees C., utilizing one of several techniques including incoherent or laser irradiation, radiofrequency waves, microwaves, or contact with warm materials or sprays of heated liquid. The heat capacity of dermatological tissue is relatively linear over this region so the energy needed to provide the second and final temperature rise of 20 degrees will be only about two thirds, or more or less, of the amount energy need to produce the same end temperature from 30 degrees starting temperature. The reduced amount of energy needed for treatment, therefore, provides the opportunity to treat a larger area and to use a smaller and safer device.

This method can also be used in conjunction with protective heat sinks or cooling devices, such as for active or passive heating or cooling that protect and modulate areas that are not targets for the treatment.

A preferred method of pre warming target tissue is to utilize selective techniques that will warm the target area or structure more than surrounding tissues to minimize collateral damage. For example in the treatment of unwanted hair, the target is the hair follicle which can be selectively heated with a range of optical wavelengths which are absorbed only by the melanin in the follicle. An ideal sequence would be:

1. Pre warm 1 to 3 mm into the target tissue or treatment area where the hair follicle is located with electromagnetic radiation of between about 600 and about 1200 um wavelength for approximately one to five seconds until the hair follicles are at 40 to 50 degrees C.
2. Cool the surface of the skin with a contact plate or dynamic cooling spray for 10 to 1000 milliseconds so as cool only the epidermis and not affect the hair follicle,
3. Irradiate the area with pulsed light of between about 600 and about 1200 nm wavelength that will selectively heat the follicle to the point of damage without affecting the surrounding tissue.

The prewarming or preheating of the target tissue can be done with a continuous source or a series of pulses that are low enough in energy as to act like a continuous source.

Since the treatment portion of the procedure only uses between about ½ and about ⅔ of the energy previously needed to damage hair follicles, such as for hair removal or for stimulation applications, temperature increase in surrounding or non-target tissue or other portions of the epidermis will likewise be reduced by as much as between about ½ and about ⅔ of what would otherwise be expected, thus minimizing the risk of burning, blistering or scarring of the superficial and top layers of skin.

The reduced energy need, therefore, to treat the target tissue, also allows use of the same power filament or other incandescent lamp operated in a pulsed fashion to treat a relatively larger area. This is a significant advantage when treating legs or backs which can take hours to treat using the 5 to 8 mm spot sizes of current systems. This invention will allow, therefore, the use of treatment spot sizes of 33 to 50% more area than possible heretofore.

The method includes treating dermatological tissue using a pulsed, non-coherent light source, such as by pulsing electric current through a filament or other portion of an incandescent lamp at a maximum potential and for a maximum time period. It will be understood that this maximum potential and/or maximum time period for the pulse rate will be determined by the materials and method of construction of the lamp. As is well know, excessive potential or current flow through a filament lamp will have a destructive effect on the lamp and its components, thereby reducing the efficiency of the procedure, and possibly causing destruction of the light source and/or other portions of the device including the lamp housing, and may cause injury to a patient being treated thereby or to those rendering such "treatment".

Figure 5:
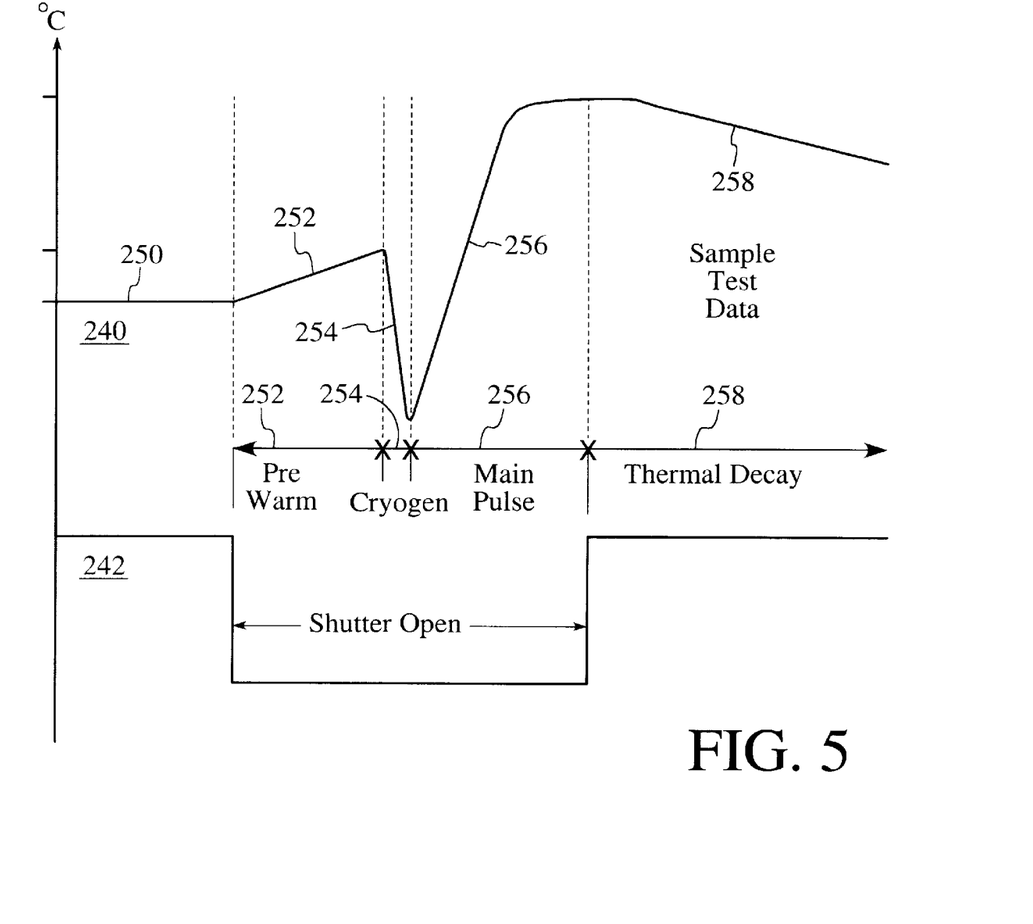

FIG. 5 is a representative schematic view of the applied voltage and resultant voltage waveform oscilloscope trace produced by the filament lamp circuit and optics of a preferred embodiment of the present invention with tissue preheating. The waveforms are representative Hewlett Packard-type oscilloscope traces produced by a thermal detector. The lower waveform 242 indicates the amount of time the shutter was open, in this case about 2.0 seconds. On the upper waveform 240, the starting temperature of the tissue indicated at 250 started to rise through region 252 and the shutter was set to close at about 50.0 degrees Celsius. Cryogen spray of about 35 milliseconds during period 254 resulted in a drop of temperature. A delay of about 30 milliseconds was allowed between the end of the cryogen spray period 54 and the treatment pulsing period 256. Treatment pulsing of the filament lamp during period 256 caused an increase in temperature of the tissue to a maximum temperature of about 50.2 degrees Celsius. Thereafter, due to the closing of the shutter, etc. thermal decay time period 258 was observed, back down to the baseline treatment temperature of about 50.0 degrees Celsius. Of the range 0 to 5 volts output, maximum output indicating a temperature of about 64 degrees Celsius, the thermal detector output of about 4.09 volts correlated with the maximum tissue temperature of 50.2 degrees Celsius.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described. All publications and patent documents referenced in this application are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treating dermatological tissue using a pulsed, filament lamp light source having a broad wavelength spectrum between about 700 nanometers and about 1800 nanometers with a substantial infrared component, the method comprising the preliminary step of preheating a target tissue to an elevated temperature below a treatment temperature, the method further comprising the steps of directing the light source at target tissue and delivering a predetermined amount of light energy thereto, the lamp being pulsed with a pulse width of between about 10 and about 1000 milliseconds, wherein the light energy induces a temperature elevation in the target tissue to the treatment temperature.

2. The method of claim 1 in which the treatment consists of shrinkage of dermatological tissue and the delivered light energy has a wavelength spectrum between about 850 and about 1800 nanometers.

3. The method of claim 1 in which the treatment consists of hair removal and the light energy directed to a hair follicle has a wavelength spectrum between about 700 and about 1000 nanometers.

4. The method of claim 1 wherein the light source comprises a filament pre-energizing circuit, the method further comprising the step of pre-energizing the filament of the light source to allow a shorter rise time in the output of the light following energization.

5. The method of claim 1 wherein the light source comprises a plurality of filter means, the method further comprising the step of selecting an appropriate wavelength spectrum from the broad spectrum output of the light source to match an effective optical absorption characteristics of the target tissue such as due to spectral absorption and anisotropic tissue scatter.

6. The method of claim 1 further comprising the step of determining the pulse width based on the thermal relaxation time of the target tissue.

7. The method of claim 1 further comprising the step of providing cooling to selected layers of the skin prior to irradiation of the target tissue.

8. The method of claim 1 further comprising the step of providing cooling to selected layers of the skin contemporaneously with irradiation of the target tissue.

9. A system for thermally treating target dermatological tissue comprising:
   means for preheating a target tissue to an elevated temperature below a treatment temperature,
   a pulsed, filament lamp treatment light source of non-laser, infrared energy providing a broad wavelength spectrum output between about 700 nanometers and about 1800 nanometers; and
   a pulse width modifier for energizing the light source with a pulse width of between about 10 and about 1000 milliseconds.

10. The system of claim 9 further comprising filter means for selecting an appropriate wavelength spectrum from the broad spectrum output of the light source to match the effective optical absorption characteristics of targeted tissue due to spectral absorption and anisotropic tissue scatter.

11. The system of claim 9 in which the light source is a tungsten lamp.

12. The system of claim 9 further comprising a reflector means for directionally reflecting the infrared light energy.

13. The system of claim 9 further comprising a switching device for switching a high current at a rapid pulse rate to the light source.

14. The system of claim 13 in which the switching device comprises an IGBT device.

15. The system of claim 9 further comprising a cooling system to provide thermal protection to the superficial layers to dermis.

16. The system of claim 15 in which the cooling system comprises a passive heat sink.

17. The system of claim 15 in which the cooling system comprises a dynamic cooling means.

18. The system of claim 9 further comprising a filament pre-energizing circuit for pre-energizing the filament of the light source to allow a short rise time in the output of the light following the pulsed energization.

19. A method for treating dermatological tissue using a pulsed, non-coherent filament lamp light source, the method including a preliminary step of preheating a target tissue to an elevated temperature below a treatment temperature, the method further including the step of pulsing electric current through the filament of the source at a predetermined potential and for a predetermined time period for treatment of target tissue.

20. The method of claim 19 in which the treatment consists of shrinkage of dermatological tissue and delivered light energy has wavelengths between about 850 and about 1800 nanometers.

21. The method of claim 19 in which an electrical current is passed through the filament of the light source prior to the pulse such that the filament is preheated prior to being pulsed.

22. The method of claim 21 in which the electrical current passed through the filament of the light source is less than that used during the treatment.

23. The method of claim 19 in which an electrical current is passed through the filament of the light source prior to the pulsing such that the rise time for the spectral output of the lamp is reduced.

24. The method of claim 23 in which the electrical current passed through the filament of the light source is less than that used during the treatment.

25. The method of claim 19 in which the light source comprises at least one filtering device for providing an altered spectral output.

26. The method of claim 25 in which the at least one filtering device provides an infrared-enhanced spectral output.

27. The method of claim 19 in which an electrical current is passed through the filament of the light source for preheating the target tissue prior to treatment.

28. The method of claim 27 in which the electrical current passed through the filament of the light source for preheating the target tissue is less than that used during treatment.

29. The method of claim 19 in which the step of preheating the target tissue comprises the use of a second, non-pulsed filament lamp light source.

30. The method of claim 19 in which the step of preheating the target tissue comprises the use of an incandescent light source.

31. The method of claim 19 in which the step of preheating the target tissue comprises the use of an infrared light source.

32. The method of claim 19 in which the step of preheating the target tissue comprises the use of a coherent light source.

33. The method of claim 19 in which the step of preheating the target tissue comprises the use of a radiofrequency source.

34. The method of claim 19 in which the step of preheating the target tissue comprises the use of a ultrasound source.

35. The method of claim 19 in which the step of preheating the target tissue comprises the use of a microwave source.

36. The method of claim 19 in which the step of preheating the target tissue comprises the use of a conductive body.

37. The method of claim 19 in which the step of preheating the target tissue comprises providing heat to superficial layers of the skin adjacent target tissue either prior to, contemporaneously with or subsequent to treatment with the pulsed filament lamp light source, as may be required.

38. The method of claim 19 further comprising the step of providing cooling to superficial layers of the skin adjacent target tissue either prior to, contemporaneously with or subsequent to treatment with the pulsed filament lamp light source, as may be required.

39. The method of claim 19 in which the pulse duration is modified by predetermined time period.

* * * * *